(12) United States Patent
Morgan

(10) Patent No.: US 7,787,959 B1
(45) Date of Patent: Aug. 31, 2010

(54) MECHANISM AND METHOD OF ATTACHING A STIMULATION AND/OR SENSING ELECTRODE TO A NERVE

(75) Inventor: Kevin L. Morgan, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 708 days.

(21) Appl. No.: 11/615,517

(22) Filed: Dec. 22, 2006

(51) Int. Cl.
*A61N 1/00* (2006.01)
(52) U.S. Cl. ........................................ 607/116; 977/904
(58) Field of Classification Search ................ 607/119, 607/116
See application file for complete search history.

(56) References Cited

U.S. PATENT DOCUMENTS

| 2004/0111141 | A1 | 6/2004 | Brabee et al. | |
|---|---|---|---|---|
| 2004/0133118 | A1 | 7/2004 | Llinas | |
| 2005/0010265 | A1* | 1/2005 | Baru Fassio et al. | 607/48 |
| 2006/0129043 | A1* | 6/2006 | Ben-Jacob et al. | 600/373 |
| 2007/0243124 | A1* | 10/2007 | Baughman et al. | 423/447.1 |
| 2007/0255320 | A1* | 11/2007 | Inman et al. | 607/2 |

FOREIGN PATENT DOCUMENTS

| WO | 2004017819 A2 | 3/2004 |
|---|---|---|
| WO | 2004052447 A1 | 6/2004 |

* cited by examiner

*Primary Examiner*—George Manuel
*Assistant Examiner*—Shubatra Narayanaswamy

(57) ABSTRACT

An attachment mechanism for creating an electrical connection between a lead and a nerve bundle is disclosed herein. The attachment mechanism includes an electrically insulative polymer material including an electrode region of the polymer material sufficiently impregnated with nanotubes to be electrically conductive.

13 Claims, 5 Drawing Sheets

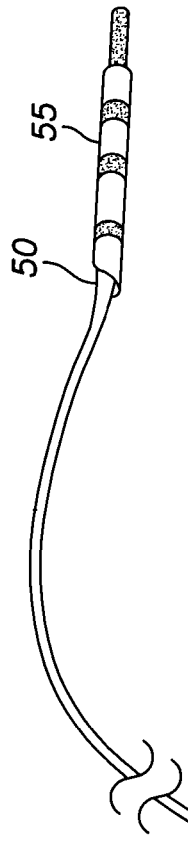
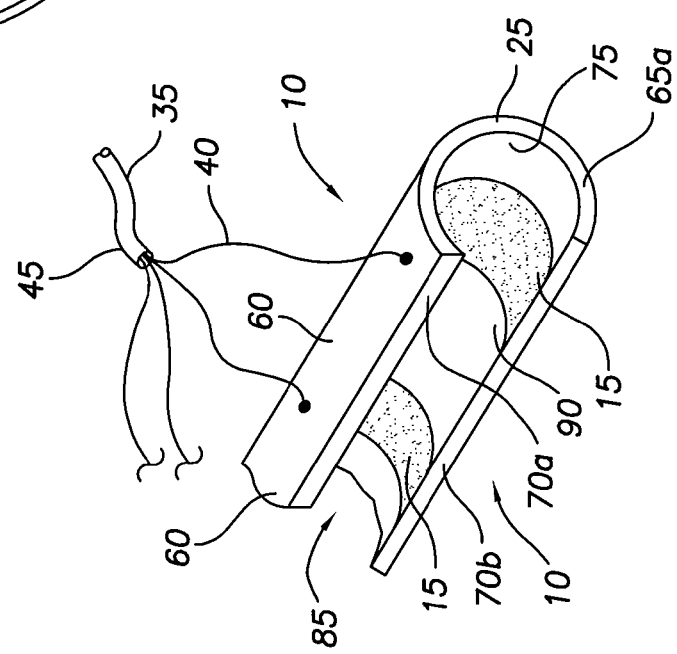
FIG. 1
FIG. 2

MECHANISM AND METHOD OF ATTACHING A STIMULATION AND/OR SENSING ELECTRODE TO A NERVE

FIELD OF THE INVENTION

The present invention relates to medical apparatus and methods. More specifically, the present invention relates to electrical nerve stimulation/sensing and mechanisms and methods for attaching a stimulation/sensing electrode to a nerve.

BACKGROUND OF THE INVENTION

Electrodes are placed around, within or adjacent to a nerve trunk or root to stimulate the nerve and/or sense electrical impulses traveling through the nerve. For example, electrodes have been applied to nerves to activate the diaphragm or bladder. Electrodes have also been applied to nerves to treat chronic back pain, blockage of neural conduction, and sensory feedback.

Although the application of electrodes to nerves has proven to be a feasible method of stimulating nerves and or sensing nerve impulses, such an electrode application has the potential to cause nerve trauma. For example, book electrodes, cuff electrodes, spiral cuff electrodes, epidural electrodes, helix electrodes, and intraneural electrodes can cause mechanical, compressive and/or other types of nerve trauma.

There is a need in the art for a mechanism that allows a stimulation and/or sensing electrode to be attached to a nerve in a manner that reduces potential nerve trauma. There is also a need in the art for a method of attaching a stimulation and/or sensing electrode to a nerve that reduces the potential for nerve trauma.

BRIEF SUMMARY OF THE INVENTION

An attachment mechanism for creating an electrical connection between a lead and a nerve bundle is disclosed herein. In one embodiment, the attachment mechanism includes an electrically insulative polymer material including an electrode region of the polymer material sufficiently impregnated with nanotubes to be electrically conductive.

A method of creating an electrical connection between a lead and a nerve bundle is disclosed herein. In one embodiment, the method includes placing an electrically insulative polymer material in contact with the nerve bundle. The polymer material includes an electrode region of the polymer material sufficiently impregnated with nanotubes to be electrically conductive.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 1 is an isometric view of a single piece, C-channel shaped attachment mechanism engaging a nerve bundle and electrically coupled to a lead body.

FIG. 2 is an enlarged isometric view of the attachment mechanism depicted in FIG. 1.

DETAILED DESCRIPTION

Figure 3:
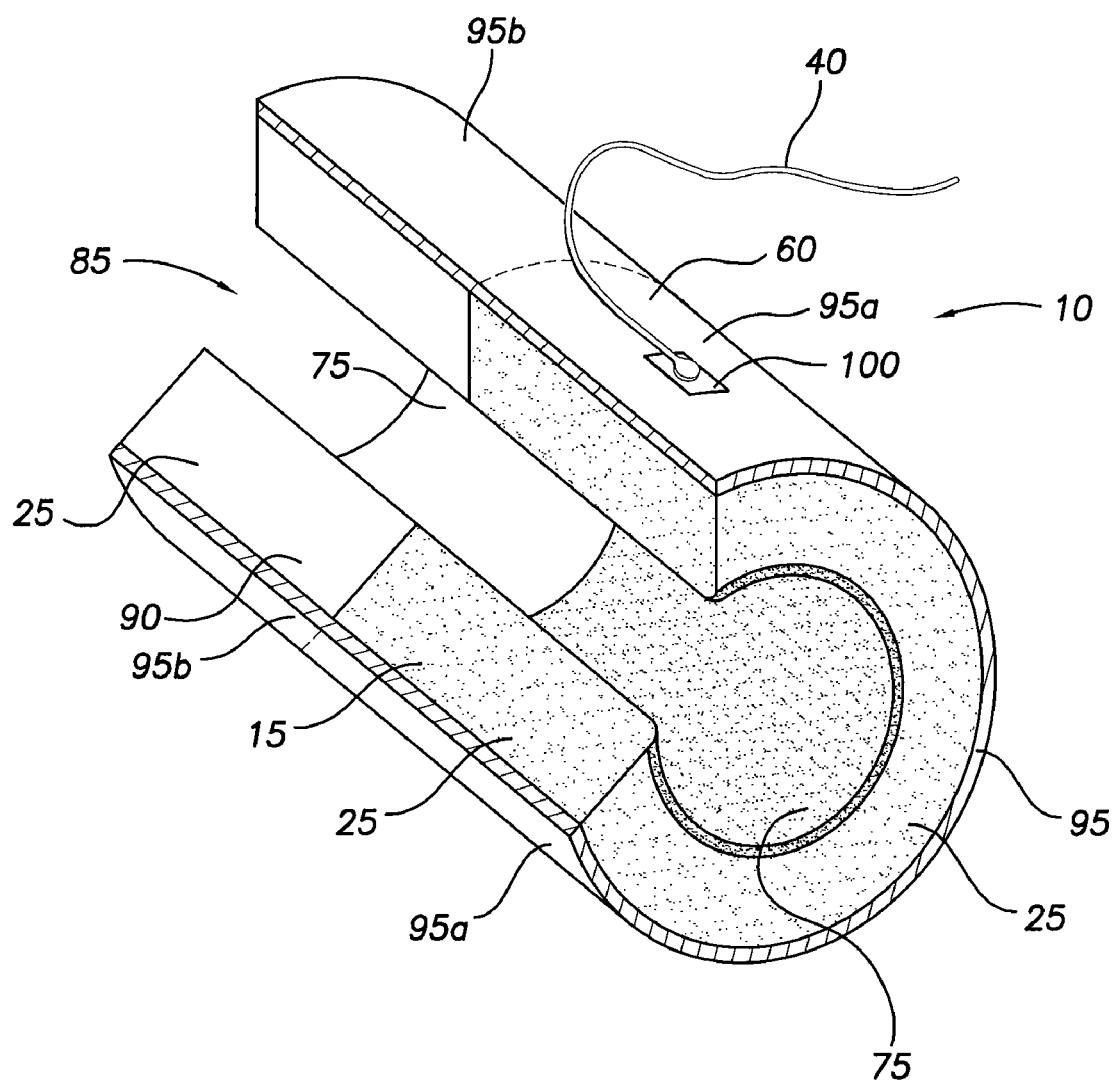
FIG. 3 is a further enlarged isometric view of a transverse or latitudinal cross section taken through an electrode portion of the attachment mechanism depicted in FIG. 2.

The present application describes various embodiments of an attachment mechanism 10 and method by which stimulation and/or sensing electrodes 15 are attached directly to a nerve bundle 20 with, as compared to prior art mechanisms and methods, a reduced likelihood of nerve trauma. In various embodiments, the attachment mechanism 10 employs an electrode 15 formed of a soft and flexible polymer material liner 25 that is impregnated or filled with nanotubes. Such electrodes 15 conform to the nerve bundle 20 to provide excellent electrical communication with the nerve bundle 20 without stressing or traumatizing the nerve bundle 20.

Figure 5:
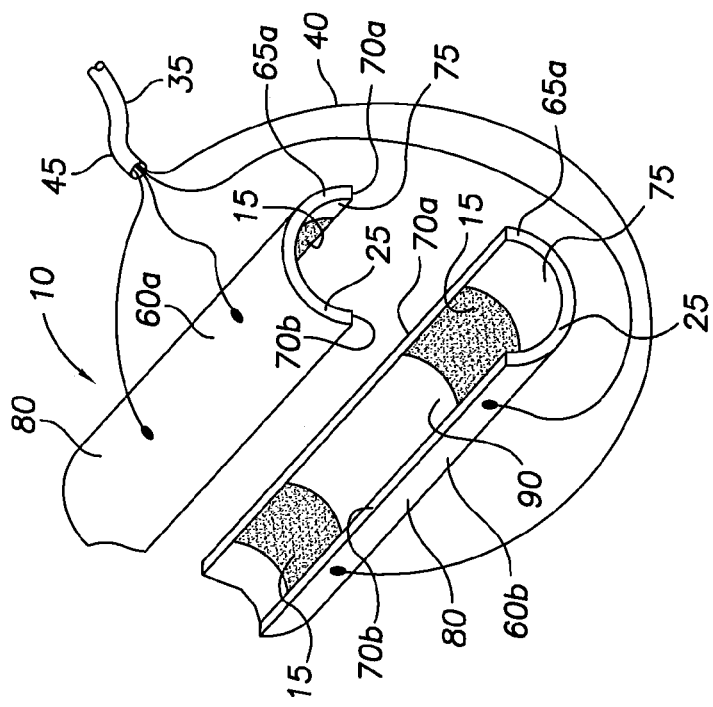
FIG. 5 is an enlarged isometric view of the one embodiment of the attachment mechanism depicted in FIG. 4.
Figure 4:
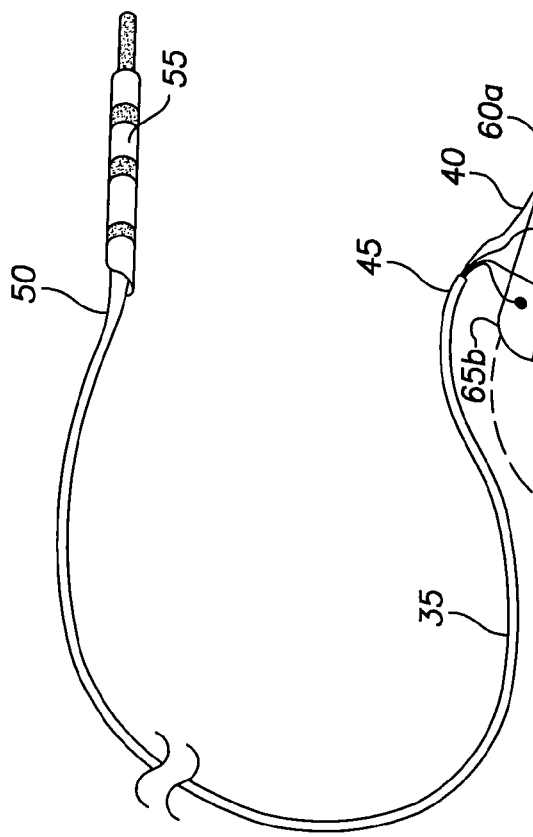
FIG. 4 is an isometric view of a two-piece, tube shaped attachment mechanism engaging a nerve bundle and electrically coupled to a lead body.
Figure 7:
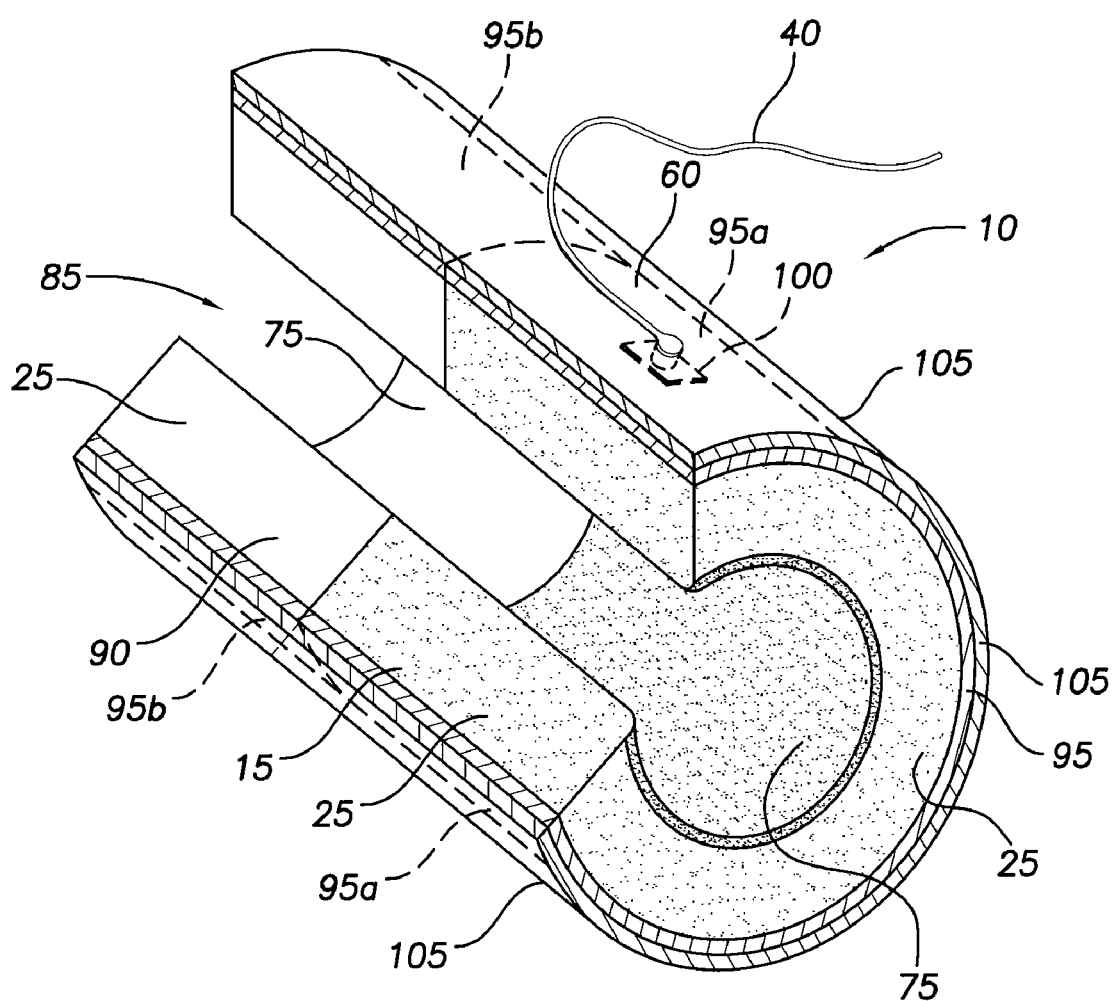
FIG. 7 is an enlarged isometric view of another embodiment of the attachment mechanism depicted in FIG. 4.

For a discussion of first and second embodiments of the attachment mechanism 10, reference is made to FIGS. 1-3 and 4-5, respectively. FIG. 1 is an isometric view of a single piece, C-channel shaped attachment mechanism 10 engaging a nerve bundle 20 and electrically coupled to a lead body 35. FIG. 2 is an enlarged isometric view of the attachment mechanism 10 depicted in FIG. 1. FIG. 3 is a further enlarged isometric view of a transverse or latitudinal cross section taken through an electrode portion 15 of the attachment mechanism 10 depicted in FIG. 2. FIG. 4 is an isometric view of a two-piece, tube shaped attachment mechanism 10 engaging a nerve bundle 20 and electrically coupled to a lead body 35. FIG. 5 is an enlarged isometric view of the one embodiment of the attachment mechanism 10 depicted in FIG. 4. FIG. 7 is an enlarged isometric view of another embodiment of the attachment mechanism 10 depicted in FIG. 4.

As indicated in FIGS. 1 and 4, in various embodiments, the attachment mechanism 10 is electrically coupled to a lead body 35 via cable conductors 40 extending from the distal end 45 of the lead body 35. The proximal end 50 of the lead body 35 terminates in a connector 55 for connecting the lead body 35 to a power source and/or sensing device. In one embodiment, the cable conductors 40 have electrically conductive cores/wires formed of electrically conductive metal or alloy materials (e.g., platinum ("Pt"), gold ("Au"), Iridium ("Ir"), platinum/iridium ("Pt/Ir") alloy, or etc.). In one embodiment, the electrically conductive cores of the cable conductors 40 are insulated with a polymer such as ethylene tetrafluoroethylene ("ETFE"), or polytetrafluoroethylene ("PTFE"). In one embodiment, the lead body 35 is a typical lead body 35 insulated with a polymer material such as silicone rubber or polyurethane. However, other biocompatible materials known in the art can be used such as silicone/polyurethane copolymers. In one embodiment, the lead body 35 has a silicone insulation and MP35N® alloy conductor wires 40.

As shown in FIGS. 1-3 and 7, in one embodiment, the attachment mechanism 10 includes a wall 60 that curves to form a C-channel type shape. The wall 60 has first and second longitudinal ends 65a, 65b, first and second longitudinally extending edges 70a, 70b, an inner circumferential surface 75 and an outer circumferential surface 80. The wall 60 curves such that the edges 70a, 70b define a slot 85 through which a nerve bundle 20 passes when the attachment mechanism 10 is being placed over or removed from the nerve bundle 20. The wall 60 is flexibly resilient such that the edges 70a, 70b can be deflected away from each other to allow the nerve bundle 20 to pass between the edges 70a, 70b and to snap back towards each other to retain the nerve bundle 20 within the attachment mechanism 10, as indicated in FIG. 1.

As indicated in FIGS. 4-5, in one embodiment, the attachment mechanism 10 is a two-piece, tubular shape 10. The attachment mechanism includes upper and lower walls 60a, 60b, which, as indicated in FIG. 5 split into two separate pieces 60a, 60b and, as depicted in FIG. 4, join together to form a tubular shape 10 through which a nerve bundle 20 extends. Each wall 60a, 60b has first and second longitudinal ends 65a, 65b, first and second longitudinally extending edges 70a, 70b, an inner circumferential surface 75 and an outer circumferential surface 80.

As indicated in FIG. 4, when the walls 60a, 60b are joined together to form the tubular shape 10, the respective edges 70a, 70b abut to form a seam 100. To allow the nerve bundle 20 to be received in the attachment mechanism 10, the walls 60a, 60b are separated as shown in FIG. 5. The nerve bundle 20 is placed in the nerve receiving area defined by the inner circumferential surface 75 of the walls 60a, 60b and the walls 60a, 60b are joined together, as indicated in FIG. 4. In one embodiment, the walls 60a, 60b are joined via an adhesive provided along the edges 70a, 70b. In other embodiments, the walls 60a, 60b are sutured, tied, wrapped or bound together via thread, tape or other tying or binding materials.

As illustrated in FIGS. 1-5 and 7, the attachment mechanism 10 includes electrodes 15 formed in a very flexible, soft polymer material liner 25. In various embodiments, the polymer material liner 25 is formed from silicone rubber, polyurethane, silicone/polyurethane copolymer, polytetrafluoroethylene (PTFE) or a combination of these or other suitable materials. As indicated in FIGS. 3 and 7, which represent the embodiment depicted in FIGS. 1 and 2, but is also applicable to the embodiment depicted in FIGS. 4 and 5, in various embodiments, the electrodes 15 are regions of the polymer material liner 25 that are sufficiently loaded with nanotubes (represented by the dots in the polymer material liner 25 depicted in FIGS. 3 and 7) to cause the electrode regions 15 of the polymer material liner 25 to be electrically conductive.

As used in this disclosure, the term "nanotube(s)" is intended to refer to nanostructures in general (i.e., any structure having nanoscale dimensions), wherein the nanostructure is formed from a material that is electrically conductive and biocompatible. Examples of such nanostructures include: substantially one dimensional so-called nanowires (or "nanowhiskers"); two dimensional, substantially planar structures such as fullerenes (e.g., a convex cage of atoms with only hexagonal and/or pentagonal faces) having a cylindrical shape; and three-dimensional structures such as the so-called buckyballs, closed- and open-ended nanotubes, multi-walled and single-walled nanotubes, and the like.

Nanotubes include any of the aforementioned nanostructures formed from carbon, boron, or any other material that is electrically conductive and biocompatible. Thus, the term nanotube(s) shall be deemed to include carbon nanotubes and other nanostructures, and shall also be deemed to cover non-carbon varieties of nanotubes made of boron and the like.

In one embodiment, for an electrode region 15, the nanotubes impregnated in the polymer material account for between approximately 0.5 percent and approximately 20 percent of the total combined weight of the polymer material liner 25 and nanotubes forming the electrode region 15. Electrode regions 15 impregnated with nanotubes to such an extent are advantageous in that they offer excellent electrical conductivity while maintaining the softness and flexibility provided by the polymer material liner 25 impregnated by the nanotubes. In one embodiment of an electrode region 15, the polymer material liner 25, which is silicone, polyurethane or silicone/polyurethane copolymer, accounts for between approximately 20 percent and approximately 80 percent of the total weight of the electrode region 15, and the carbon or boron nanotubes impregnating the polymer material liner 25 of the electrode region 15 account for between approximately 20 percent and approximately 80 percent of the total weight of the electrode region 15.

As shown in FIGS. 1-5 and 7, in various embodiments, the electrodes 15 are provided in a spaced-apart configuration along the length of the polymer material liner 25. In other words, each electrode region 15 is separated from the adjacent electrode region 15 by a region of the polymer material liner 25 that is not loaded with nanotubes (i.e., a non-nanotube loaded region 90).

As can be understood from FIGS. 1-2 and 4-5 and more specifically depicted in FIGS. 3 and 7, a flexible backing 95 forms the outer circumferential surface of the attachment mechanism 10, and the polymer material liner 25 adheres to the inner circumferential surface of the backing 95. The inner circumferential surface 75 of the polymer material liner 25 forms a nerve contacting or engaging surface 75.

As can be understood from FIG. 3, in one embodiment, the backing 95 is formed from a flexible polymer. Candidate polymers include polyurethane, silicone rubber, or silicone/polyurethane copolymer. The polymer flexible backing 95 insulates the electrode regions 15 from the tissue surrounding the nerve to which the mechanism 10 is attached. Also, the polymer flexible backing 95 allows the attachment mechanism 10 to expand and spring back due to the elastic qualities of the polymers.

As can be understood from FIG. 7, in another embodiment, the flexible backing 95 is formed of a malleable, biocompatible metal or metal alloy. Candidate metals or metal alloys include Pt, Au, Ir, Pt/Ir alloy, etc. The metal or metal alloy flexible backing 95 allows the attachment mechanism 10 to be expanded and held in that shape while the nerve is being carefully placed into the circumferential surface 75. The attachment mechanism 10 can then be returned to a closed position by squeezing the mechanism 10.

In one embodiment, as shown in FIG. 7, which represents the embodiment depicted in FIGS. 1 and 2, but is also applicable to the embodiment depicted in FIGS. 4 and 5, the backing 95 is formed of electrically conductive portions 95a and electrically insulative portions 95b. The electrically conductive backing portions 95a serve as the backing 95 for the electrode regions 15 of the polymer material liner 25 and are formed from one of the aforementioned electrically conductive metal or alloy materials. An insulative polymer layer 105 extends over the outer circumferential surface of the backing 95 to insulate the backing portion 95 from the tissue surrounding the nerve 20 to which the mechanism 10 is attached. The electrically insulative backing portions 95b serve as the backing 95 for the non-electrically conductive regions 90 of the polymer material liner 25 and to electrically separate adjacent electrically conductive backing portions 95a. In one embodiment, the electrically insulative backing portions 95b are formed from an electrically insulative polymer material, such as silicone rubber, polyurethane, silicone/polyurethane copolymers, PTFE, or polysulfone.

As shown in FIG. 7, in one embodiment, the conductor 40 extends through the insulative layer 105 to couple to a transition pad 100 below the insulative layer 105. The transition pad 100 is electrically coupled to the electrically conductive backing portion 95a.

In one embodiment, as shown in FIG. 3, which represents the embodiment depicted in FIGS. 1 and 2, but is also applicable to the embodiment depicted in FIGS. 4 and 5, the backing 95 is formed of electrically insulative backing portions 95a, 95b. The electrically insulative backing portions 95a, 95b serve as the backing 95 for the electrode regions 15 of the polymer material liner 25 and are formed from one of the aforementioned electrically insulative materials. The electrically insulative insulate the electrode regions 15 from the tissue surrounding the nerve 20 to which the mechanism 10 is attached.

As depicted in FIGS. 1, 2, 4 and 5, and more specifically FIG. 3, wherein the flexible backing 95 is formed of an electrically insulative polymer, a distal end of a wire conductor 40 electrically couples with the electrode region 15 for the transfer of electrical energy between the electrode region 15 and the wire conductor 40. More specifically, as indicated in FIG. 3, in one embodiment, a conductor 40 electrically couples to the electrode region 15 through an electrically conductive transition pad 100 located on the electrically insulative polymer flexible backing portion 95a. The electrically conductive transition pad 100 extends through the polymer flexible backing 95 to electrically couple the conductor 40 to the electrode region 15. The electrical couple between the transition pad 100, conductor 40, and electrode region 15 is created by welding, soldering, mechanical methods (e.g., crimping, fasteners, etc.), or epoxies and adhesives. The electrical couple allows electrical continuity to be established between the conductor 40 and electrode region 15.

As shown in FIG. 7, wherein the portions of the backing 95 are electrically conductive, a distal end of a wire conductor 40 extends through the electrically insulative layer 105 to electrically couple with the electrically conductive backing portion 95a in the region of the backing 95 that that contacts an electrode region 15. The electrical couple between a conductor 40 and the backing 95 is formed via welding, soldering mechanical methods (e.g., crimping, fastening, etc.) or electrically conductive epoxies. The metal backing portions 95a are malleable enough to allow the attachment mechanism 10 to open and close sufficiently when a nerve 20 is placed in the inner circumferential surface 75. The insulating layer 105 extends over the metal backing 95 to insulate the electrically conductive backing portions 95a from the tissue surrounding the nerve 20 to which the mechanism 10 is attached.

As can be understood from FIGS. 1-5 and 7, an electrical current traveling to or from the nerve bundle 20 passes through the electrode region 15, which is loaded with electrically conductive nanotubes and is electrically coupled to the backing 95. In use, an attachment mechanism 10 receives a nerve bundle 20 such that the inner circumferential surface 75 of the polymer material liner 25 substantially surrounds and abuts against the outer circumferential surface of the nerve bundle 20. Where the backing 95 is electrically insulative, as depicted in FIG. 3, a stimulation electrical current travels through the lead body 35, the conductors 40, the electrode region 15 of the polymer material liner 25, and into the portion of the nerve bundle 20 contacting the electrically conductive electrode region 15. Where backing portions 95a are electrically conductive, as indicated in FIG. 7, a stimulation electrical current travels through the lead body 35, the conductors 40, the conductive backing portion 95a, the electrode region 15 of the polymer material liner 25, and into the portion of the nerve bundle 20 contacting the electrically conductive electrode region 15.

As can be understood from FIGS. 3 and 7, electrical nerve impulses travel along paths similar to, but reversed from, the paths described above with respect to FIGS. 3 and 7. Specifically, the electrical nerve impulses travel from the nerve bundle 20 to a sensing device coupled to the connector 55 at the proximal end 50 of the lead body 35. Thus, the attachment mechanism 10 can be used for delivering stimulation electricity to a nerve bundle or to sense electrical nerve impulses.

As can be understood from FIGS. 1-5, in various embodiments, one or more electrode regions 15 will serve as working electrodes, while one or more other electrode regions 15 will serve as counter electrodes. In one embodiment, all electrode regions 15 serve as working electrodes, and the counter electrode is provided by an electrode mounted on the lead body 35 or provided elsewhere on/in the patient (e.g., via an electrically conductive patch placed on/in the patient). In one such embodiment where all electrode regions 15 serve as working electrodes, the backing 95 can be entirely electrically conductive and will not have non-electrically conductive portions 95b.

As can be understood from FIGS. 4 and 5, in one embodiment, one wall section 60a will severe as the working electrode and the other wall section 60b will serve as the counter electrode. In one such embodiment, to prevent the working and counter electrodes from shorting out, the edges 70a, 70b of the wall sections 60a, 60b are joined together via an electrically insulative epoxy or adhesive that forms an electrically insulative layer between the electrodes 15 of the wall sections 60a, 60b.

The attachment mechanisms 10 depicted in FIGS. 1-5 are advantageous in that their shapes/configurations and the softness of their polymer material liners 25 allow intimate connections with the nerve bundles 20 with a reduced likelihood of nerve bundle trauma. The non-traumatic, intimate connections combined with the electrical conductivity of the electrode regions 15 result in nerve bundle attachment mechanisms 10 that provide (1) optimal stimulation performance without current leakage and (2) sensitivity that is able to sense minute electrical activity that would normally be covered by artifacts (e.g., muscle movement, heart activity, breathing, radio waves, static, etc.). To further minimize current leakage and/or the impact of artifacts, in various embodiments, the backing 95 is formed from Pt, Au, etc., which acts as a shielding material.

In various embodiments, the polymer material liner 25 is formed or molded onto, extruded over, or formed and affixed to the inner circumferential surface of the backing 95. In one embodiment, the electrode regions 15 and insulative regions 90 of the polymer material liner 25 are applied via one of the aforementioned methods in a single continuous piece. In one embodiment, the electrode regions 15 and insulative regions 90 of the polymer material liner 25 are applied individually via one of the aforementioned methods.

Figure 6:
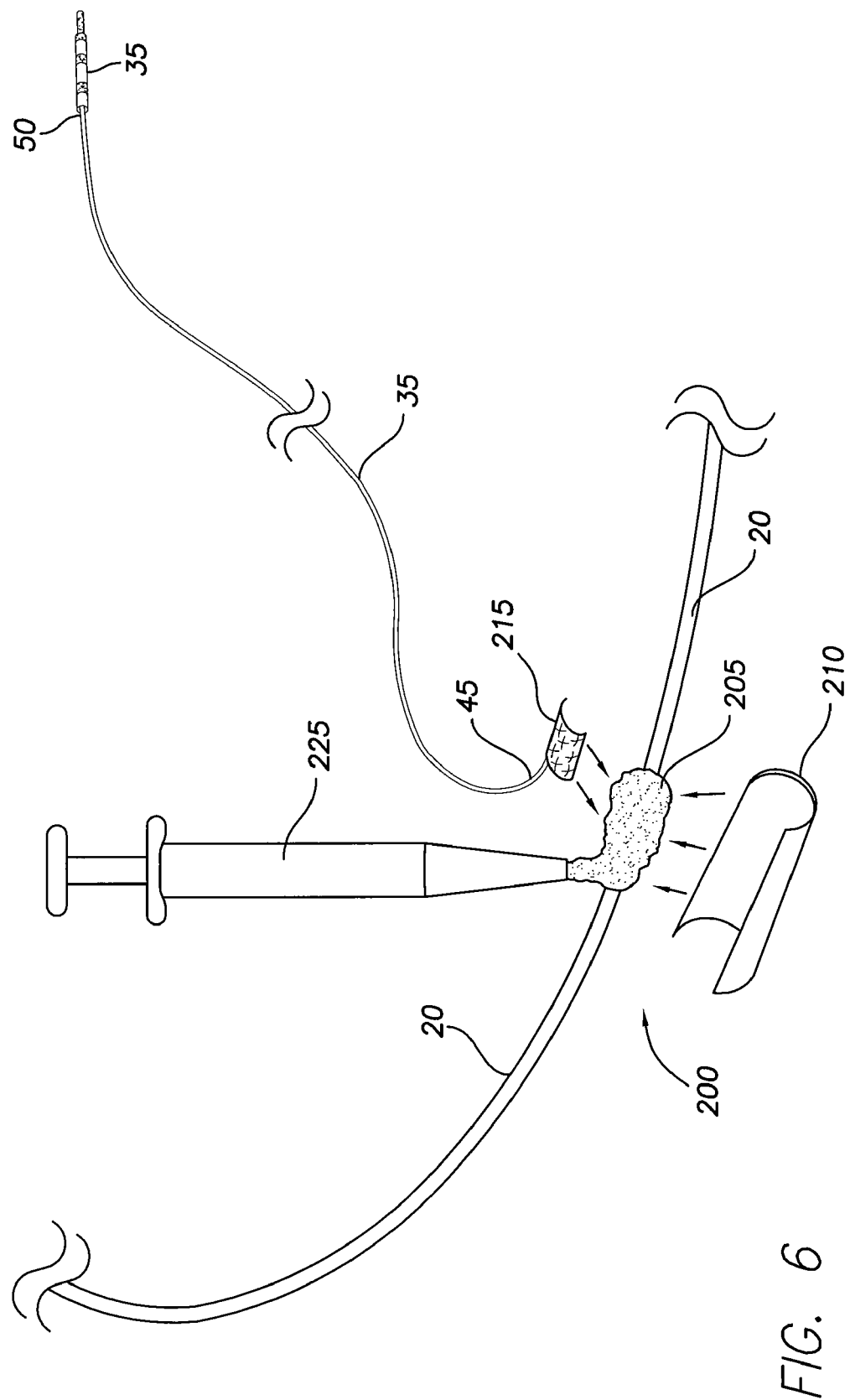
FIG. 6 is an isometric view of a fluid or gel-like attachment mechanism engaging a nerve bundle and electrically coupled to a lead body.

For a discussion of a third embodiment of the attachment mechanism 10, reference is made to FIG. 6, which is an isometric view of a fluid or gel-like attachment mechanism 200 engaging a nerve bundle 20 and electrically coupled to a lead body 35. As shown in FIG. 1, in one embodiment, the fluid or gel-like attachment mechanism 200 includes a soft biocompatible polymer material 205 such as silicone, silicone gel, or medical adhesive (silicone RTV), a flexible backing 210, and a conductive mesh 215. The distal end 45 of the lead 35 electrically couples to the mesh 215, and the lead 35 includes a connector 55 at its proximal end 50 and is similar to those already described with respect to FIGS. 1-5.

As can be understood from FIG. 6, in one embodiment, the polymer material 205 is applied in a liquid or gel-like form to the nerve bundle 20. In one embodiment, the polymer material 205 is applied via a syringe-like device 225. In other embodiments, the polymer material 205 is applied by being dabbed or painted onto the nerve bundle 20.

In one embodiment, the mesh 215 is applied to the liquid or gel-like polymer material 205 and, as the polymer material 205 solidifies about the nerve bundle 20, the material 205 also solidifies to the mesh 215. In one embodiment, the mesh 215 is formed of an electrically conductive biocompatible material such as platinum, titanium, stainless steel, or nitinol.

In one embodiment, the backing 210, which is similar to the backing 95 described with respect to FIGS. 1-5, is wrapped about the polymer material 205 and mesh 215. As the material 205 solidifies about the nerve bundle 20, the material 205 solidifies to the backing 210.

In one embodiment, no mesh 215 is provided. Instead, a backing 210, which is electrically coupled to the lead body 35 via conductors 40 as depicted in FIGS. 1-5, is wrapped about the polymer material 205. In one embodiment, this backing 210 is configured as discussed with respect to FIGS. 1-5.

In one embodiment, the polymer material 205 is impregnated with nanotubes (represented by the dots in the polymer material 205 depicted in FIG. 6) of the types and in the concentrations as previously discussed with respect to FIGS. 1-5. As indicated in FIG. 6, in one embodiment, the entirety of the polymer material 205 is impregnated with nanotubes such that the entire polymer material 205 is an electrode. In other embodiments, the polymer material 205 has zones or regions that are impregnated with nanotubes (thereby forming electrodes) and zones or regions that are not impregnated with nanotubes (thereby forming electrically insulative zones or regions).

In one embodiment, a multiple orifice syringe-like device is used to simultaneously deposit nanotube impregnated and nanotube-free polymer materials 205 adjacent to each other, thereby forming adjacent electrode zones and electrically insulative zones, respectively. In one embodiment, the electrode zones are electrically coupled to respective electrically conductive meshes 215. In one embodiment, the electrode zones are electrically coupled to respective electrically conductive portions of the backing 210, as described with respect to certain embodiments relating to FIGS. 1-5. In one embodiment, some electrodes will be working electrodes and other electrodes will be counter electrodes.

In one embodiment, the electrode zones are first deposited about the nerve bundle 20 in a spaced apart configuration, and the insulative zones are then deposited in the spaces between the electrode zones. The electrode zones are then coupled to the lead body 35 as already described and some of the electrode zones will be working electrodes and others will be counter electrodes. In other embodiments, the aforementioned process is reversed.

The attachment mechanism 200 describe above with respect to FIG. 6 is advantageous in that is provides a non-traumatic method of achieving excellent electrical communication between the nerve bundle 20 and the lead body 35. This electrical communication is applicable to both nerve impulse sensing and electrical stimulation of nerves. The liquid or gel application of the polymer material 205 allows for the attachment mechanism 200 to be coupled to nerve bundles 20 having very small diameters.

The attachment mechanism 10, 200 depicted in FIGS. 1-6 are advantageous in that the polymer material liner 25, 205 allows a small amount of nerve bundle movement within the attachment device 10, 200 to lessen the stress on the nerve bundle 20. Furthermore, in various embodiments, the polymer material liner 25, 205 give full circumferential contact with the nerve bundle 20 for optimal electrode performance and reduced interference of artifacts.

Although the present invention has been described with reference to preferred embodiments, persons skilled in the art will recognize that changes may be made in form and detail without departing from the spirit and scope of the invention.

What is claimed is:

1. An attachment mechanism for creating an electrical connection between a lead and a nerve bundle, the attachment mechanism comprising:
   an electrically insulative polymer material configured to attach to the nerve bundle, the polymer material including an electrode region of the polymer material sufficiently impregnated with nanotubes to be electrically conductive; and
   an electrically conductive layer extending over an outer surface of the polymer material;
   wherein the conductive layer and polymer layer are curved, the polymer layer forming an inner circumferential surface.

2. The attachment mechanism of claim 1, wherein the electrode region is electrically coupled to the conductive layer.

3. The attachment mechanism of claim 2, further comprising an insulative layer extending over an outer surface of the conductive layer.

4. The attachment mechanism of claim 1, wherein the conductive layer is configured to be electrically coupled to the lead.

5. The attachment mechanism of claim 1, wherein the attachment mechanism is in the form of a C-channel.

6. The attachment mechanism of claim 1, further comprising an electrically insulative layer extending over an outer surface of the polymer.

7. The attachment mechanism of claim 6, further comprising a transition pad on the electrically insulative layer and electrically coupled to the electrode region, wherein the lead is electrically coupled to the transition pad.

8. The attachment mechanism of claim 6, wherein the electrically insulative layer is curved, the polymer layer forming an inner circumferential surface.

9. The attachment mechanism of claim 8, wherein the attachment mechanism is in the form of a C-channel.

10. An attachment mechanism for creating an electrical connection between a lead and a nerve bundle, the attachment mechanism comprising: an electrically insulative polymer material including an electrode region of the polymer material sufficiently impregnated with nanotubes to be electrically, wherein the polymer material is applied to the nerve bundle in a liquid or gel form.

11. The attachment mechanism of claim 10, further comprising an electrically conductive mesh adhered to the polymer material and electrically coupled to the lead.

12. A method of creating an electrical connection between a lead and a nerve bundle, the method comprising: placing an electrically insulative polymer material in contact with the nerve bundle in such a manner that the polymer material attaches to the nerve bundle, wherein the polymer material includes an electrode region of the polymer material sufficiently impregnated with nanotubes to be electrically conductive, and wherein placing the electrically insulative polymer material in contact with the nerve bundle comprises applying the polymer material to the nerve bundle in a liquid or gel form.

13. A method of creating an electrical connection between a lead and a nerve bundle, the method comprising: placing an electrically insulative polymer material in contact with the nerve bundle in such a manner that the polymer material attaches to the nerve bundle, wherein the polymer material includes an electrode region of the polymer material sufficiently impregnated with nanotubes to be electrically conductive, and wherein placing the electrically insulative polymer material in contact with the nerve bundle comprises resiliently deforming the polymer material to at least partially encircle the nerve bundle with the polymer material.

* * * * *